United States Patent [19]

Neef et al.

[11] 4,155,923
[45] May 22, 1979

[54] PROCESS FOR THE PREPARATION OF 17β-HYDROXY-20-ALKOXYPREGNANE-21-OIC ACID DERIVATIVES

[75] Inventors: Günter Neef; Gregor Haffer; Ulrich Eder; Gerhard Sauer; Rudolf Wiechert, all of Berlin, Fed. Rep. of Germany

[73] Assignee: Schering Aktiengesellschaft, Berlin and Bergkamen, Fed. Rep. of Germany

[21] Appl. No.: 873,444

[22] Filed: Jan. 30, 1978

[30] Foreign Application Priority Data

Jan. 28, 1977 [DE] Fed. Rep. of Germany ....... 2704130

[51] Int. Cl.² ............................................. C07J 7/00
[52] U.S. Cl. ...................... 260/397.1; 260/239.55 C; 260/397.47; 260/397.5
[58] Field of Search ....................................... 260/397.1

[56] References Cited

FOREIGN PATENT DOCUMENTS 1468646 1/1967 France ................................. 260/397.4
504424 4/1971 Switzerland .......................... 260/397.4

Primary Examiner—Ethel G. Love
Attorney, Agent, or Firm—Millen & White

[57] ABSTRACT

A process for the preparation of 17β-hydroxy-20-alkoxypregnane-21-oic acid derivatives of the formula

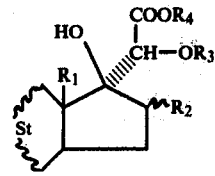

wherein
$R_1$ is methyl or ethyl;
$R_2$ is hydrogen or methyl, either being in the α- or β-position;
$R_3$ is lower alkyl of 1–4 carbon atoms;
$R_4$ is alkyl of 1–8 carbon atoms or benzyl; and
St is the residue of a steroid ABC ring system;
comprises reacting (a) a 17-oxo compound of the formula

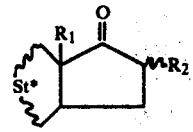

wherein
$R_1$ and $R_2$ are as defined above and
St* is said steroid ABC ring system residue, St, in a form which is chemically compatible with said reaction;
with (b) an enolate ion of an alkoxyacetic acid alkyl ester of the formula

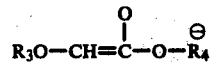

wherein $R_3$ and $R_4$ are as defined above.

10 Claims, No Drawings

PROCESS FOR THE PREPARATION OF 17β-HYDROXY-20-ALKOXYPREGNANE-21-OIC ACID DERIVATIVES

BACKGROUND OF THE INVENTION

The present invention relates to a novel process for the preparation of 17β-hydroxy-20-alkoxypregnane-21-oic acid derivatives.

SUMMARY OF THE INVENTION

The present invention relates to a novel process for the preparation of 17β-hydroxy-20-alkoxypregnane-21-oic acid derivatives of Formula I

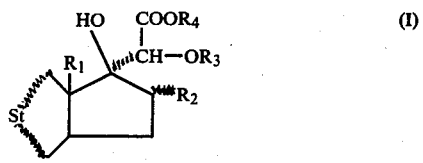

wherein
$R_1$ is methyl or ethyl,
$R_2$ is hydrogen or methyl, either one being in the α- or β-position.
$R_3$ is lower alkyl of 1–4 carbon atoms,
$R_4$ is alkyl of 1–8 carbon atoms or benzyl, and
St is the residue of a steroid ABC ring system which comprises reacting a compound of Formula II

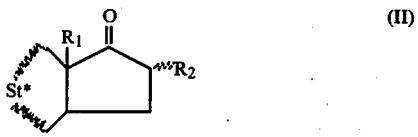

wherein $R_1$ and $R_2$ are as defined above and St* is said steroid ABC ring system residue, St, in a form which is chemically compatible with the reaction, e.g., is the same as St except that optionally present keto groups are blocked intermediarily,
with an enolate ion of an alkoxyacetic acid alkyl ester of Formula III

wherein $R_3$ and $R_4$ are as defined above.

DETAILED DISCUSSION $R_3$ is lower alkyl of 1–4 carbon atoms, such as, for example, methyl, ethyl, propyl, butyl, isobutyl, etc. Methyl is preferred.

Suitable alkyl residues $R_4$ include, for example: methyl, ethyl, propyl, isopropyl, butyl, sec-butyl, tert-butyl, pentyl, hexyl, and octyl. Preferred for $R_4$ are methyl and ethyl.

St refers to the residue of the ABC ring of an optionally substituted steroid molecule optionally having 1–4 double bonds. Suitable substituents of the steroid residue St include, for example: fluorine or chlorine; methyl; free, esterified, or etherified hydroxy groups (in particular alkoxy groups of 1–6 carbon atoms in the alkyl residue, tetrahydropyranyloxy groups, benzyloxy groups, alkanoyloxy groups of 1–8 carbon atoms in the alkanoyl residue, and benzoyloxy groups); and free or ketalized oxo groups (particularly alkylidenedioxy groups of 2–6 carbon atoms in the alkylidene residue and o-phenylenedioxy groups). Suitable positions for such substituents include for example the 1, 2, 3, 4, 6, 9 or 11 position.

Suitable unsaturated steroid residues include, for example: steroid residues having a $\Delta^4$-double bond and those with $\Delta^{1,4}$-, $\Delta^{4,6}$-, $\Delta^{4,9(11)}$-, $\Delta^{1,4,9(11)}$-double bonds; steroid residues having a $\Delta^5$-double bond or $\Delta^{5,9(11)}$-double bonds; steroid residues with $\Delta^{1,3,5(10)}$- or $\Delta^{1,3,5(10),9(11)}$-double bonds; and steroid residues with a $\Delta^3$-double bond or with $\Delta^{2,5(10)}$-, $\Delta^{2,5(10),9}$-, $\Delta^{3,5}$-, and $\Delta^{3,5,9(11)}$-double bonds.

In view of the commercial usefulness of the products of the process of this invention, which are valuable intermediates for the synthesis of steroid hormones, e.g., corticoides
preferred starting compounds are those 17-oxo steroids of general Formula II carrying a steroid residue of the partial Formulae St$_1$ through St$_6$

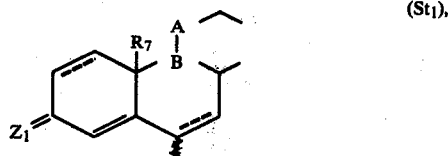

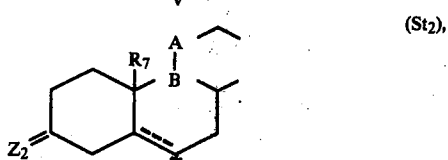

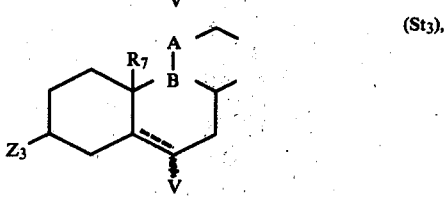

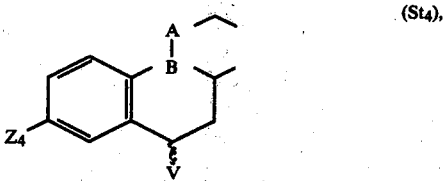

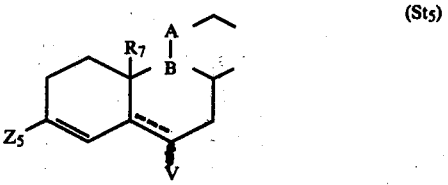

or

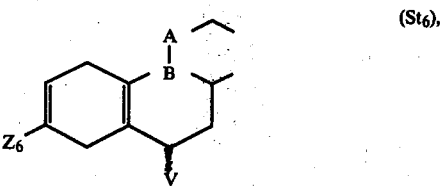

wherein
the grouping —A—B— is a —CH$_2$—CH<, —CHF—CW<, —CHCl—CW<, —CHOH—CW<,

—CO—CW<, or —CH=C<-group wherein W is hydrogen, fluorine, or chlorine;

V is hydrogen, methyl, or fluorine;

$Z_1$ is free or ketalized oxo;

$Z_2$ is ketalized oxo;

$Z_3$ and $Z_4$ each is free, esterified, or etherified hydroxy;

$Z_5$ and $Z_6$ each is etherified hydroxy;

$R_7$ is hydrogen or methyl; and the bonds, - - - -, are single bonds or double bonds.

Suitable oxo groups for $Z_1$ and $Z_2$ include preferably o-phenylenedioxy and alkylenedioxy of 2-6 carbon atoms in the alkylene residue. Examples of such suitable alkylenedioxy groups are: the ethylenedioxy group, the 1,3-propylenedioxy group, the 2,3-butylenedioxy group, and the 2,2-dimethylpropylenedioxy group.

Suitable esterified hydroxy groups for $Z_3$ and $Z_4$ include preferably benzoyloxy or a straight-chain or branched alkanoyloxy of 1-8 carbon atoms in the alkanoyl residue. Examples of such alkanoyloxy groups are: formyloxy, acetoxy, propionyloxy, dimethylacetoxy, trimethylacetoxy, butyryloxy, tert-butyl-acetoxy, hexanoyloxy and octanoyloxy.

Suitable etherified hydroxy groups for $Z_3$, $Z_4$, $Z_5$ or $Z_6$ include preferably benzyloxy, tetrahydropyranyloxy, and straight-chain or branched alkoxy of 1-6 carbon atoms in the alkyl residue. Examples of such alkoxy groups are: methoxy, ethoxy, propoxy, isopropoxy, butoxy, isobutoxy, sec-butoxy, and tert-butoxy.

The nature of the St residue is not critical to the process of this invention. It is simply required that the St moiety be chemically compatible with the reaction conditions employed. Toward this end, for example, potentially troublesome groups, such as oxo groups other than that in the 17-position, can be blocked in accordance with fully conventional procedures. For example, suitable blocking (protecting) groups for oxo moieties include for example alkylenedioxy groups e.g., methylenedioxy, ethylenedioxy, alkylidenedioxy groups e.g., 1,3-propylenedioxy, 2-methyl-1,3-propylenedioxy, 2,2-dimethylpropylidenedioxy and o-phenylenedioxy groups.

The starting material enolate ion is formed in fully conventional fashion from the corresponding alkoxyacetic acid alkyl ester in an inert solvent with an anhydrous base as described for example in (Tetrahedron Letters, 1975, 1477).

Especially suitable anhydrous bases include lithium salts of sterically hindered amines, such as, for example, of diisopropylamine.

Particularly suitable enolate ions for the reaction include those of methoxyacetic acid alkyl esters. Quite especially preferred is the enolate ion of the methyl ester of methoxyacetic acid.

The process of this invention represents a very simple industrial method for the buildup of steroid side chains. In accordance therewith, using techniques well known to those skilled in the art, the enolate ion of an alkoxyacetic acid alkyl ester is simply chemically added to a 17-keto steroid. Surprisingly, the desired compounds can be isolated almost quantitatively without expensive separating operations.

The reaction is conducted in an inert solvent at temperatures of −80° to −20° C., preferably at temperatures of −78° to −50° C. Inert solvents suitable for the reaction include, for example, THF, dioxane, hexane, pentane, dimethoxyethane, and the like. The order of mixing of the two reactants is not critical and either may be added to the other. Similarly, pressure and the nature of the ambient atmosphere are not critical. Atmospheric pressure is suitable and preferred. The two reactants are suitably reacted in stoichiometric proportions but excesses of one or the other may be employed with no harmful effects. Suitable times of reaction are 2-20 hours, preferably 2-6 hours. Stirring of the reaction medium is optional.

The 17β-hydroxy-20-alkoxypregnane-21-oic acid derivative obtained as a product of the process of this invention can be further processed without purification of the crude product. For example, it is possible to synthesize 17,20-enol ethers in very good yields from 17β-hydroxy-20-alkoxypregnane-21-oic acid derivatives according to known dehydration methods, such as, for example, by reacting thionyl chloride with pyridine. In DOS [German Unexamined Laid-Open Application] No. 2,361,682, 17,20-enol ethers are produced according to the Wittig-Horner process. However, this method is industrially useless since the dialkylphosphonoalkoxyacetic acid alkyl ester necessary for the reaction can be synthesized only with great expense by way of a multistage procedure (W. Grell and H. Machleidt, Lieb. Ann. Chem. 699: 53 [1966]). Moreover, the 17,20-enol ethers prepared according to the Wittig-Horner process must be purified by chromatography, whereas the 17,20-enol ethers produced in accordance with the process of the present invention can be further processed after only a one-time recrystallization.

As another example, the 17β-hydroxy-20-alkoxypregnane-21-oic acid derivatives which are obtained according to this invention can be reduced to the corresponding 21-alcohols also by following fully conventional methods. The 21-alcohols can be esterified under the customary conditions to obtain the corresponding 21-ester derivatives, such as, for example, the 21-acetoxy derivatives. If the 21-ester is dehydrated, for example, with methanesulfonic acid chloride/triethylamine, the corresponding $\Delta^{16}$-compound is obtained. This reaction can be conducted under the usual conditions, for example, at temperatures of −30° to 0° C. in inert solvents, such as, for example, methylene chloride. The subsequent cleavage of the $\Delta^{16}$,20-ethers, saponification, and oxidation lead to production of $\Delta^{16}$,20-keto compounds which are not accessible by way of the Wittig-Horner reaction.

Accordingly, it is possible with the aid of the process of this invention to prepare, in an almost quantitative yield, intermediates which can be further processed to prepare pharmacologically active compounds. Thus, it is possible, for example, to convert 17,20-enol ethers, by following conventional methods, into 20-ketopregnene-21-oic acid derivatives having an anti-inflammatory effect, such as, for example, 6α-fluoro-11β-hydroxy-3,20-dioxo-16α-methyl-1,4-pregnadiene-21-oic acid butyl ester. It is, for example, also possible to convert $\Delta^{16}$,20-keto steroids to 16α, 17α-dihydroxy-20-keto steroids, such as triamcinolone, for example.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The temperatures in the examples are set forth in degrees Celsius.

EXAMPLE 1

Methyl Ester of 3β-Ethoxy-17β-hydroxy-20-methoxy-5-pregnene-21-oic Acid

At −78°, a solution of 10 g. of the methyl ester of methoxyacetic acid in 20 ml. of THF is added dropwise to a solution of lithium diisopropylamide (from 11 g. of diisopropylamine in 100 ml. of tetrahydrofuran and 46 ml. of a 15% solution of n-butyllithium in hexane); the reaction mixture is agitated for 15 minutes at this temperature. Then, 5 g. of 3β-ethoxy-5-androsten-17-one in 20 ml. of THF is added dropwise thereto and the mixture is stirred for another 3 hours at −78°.

In order to work up the reaction mixture, the latter is combined dropwise with 30 ml. of saturated $NH_4Cl$ solution at −60°, then poured into approximately 500 ml. of water, and extracted with ethyl acetate.

Yield: 6.7 g. of 3β-ethoxy-17β-hydroxy-20-methoxy-5-pregnene-21-oic acid methyl ester as a mixture of the C-20 isomers. The crude product can be used in the subsequent reactions as the mixture of epimers.

By chromatography on about 350 g. of silica gel with petroleum ether/acetone 0–15%, the following compounds are obtained in the elution sequence:
5.6 g. 20R-epimer, m.p. 122°–124°
0.6 g. 20S-epimer, m.p. 192°–193°

EXAMPLE 2

Methyl Ester of 3β-Ethoxy-20-methoxy-5,17(20)-pregnadiene-21-oic Acid

A solution of 4.0 g. of the methyl ester of 3β-ethoxy-17β-hydroxy-20-methoxy-5-pregnene-21-oic acid (C-20 epimer mixture) in 20 ml. of pyridine is combined under ice cooling dropwise with 2 ml. of thionyl chloride and then agitated for 30 minutes at 5°–10°. To work the reaction mixture up, it is poured into 200 ml. of water, extracted with ethyl acetate, the ethyl acetate phases washed with 2N HCl and saturated NaCl solution, dried over $Na_2SO_4$, and concentrated. Crystallization from diisopropyl ether yields 3.2 g. of the methyl ester of 3β-ethoxy-20-methoxy-5,17(20)-pregnadiene-21-oic acid, m.p. 117°–119°.

EXAMPLE 3

Methyl Ester of 17β-Hydroxy-3,20-dimethoxy-3,5-pregnadiene-21-oic Acid

Under the conditions described in Example 1, 15 g. of 3-methoxy-3,5-androstadien-17-one is reacted with the lithium enolate of the methyl ester of methoxyacetic acid. After recrystallization of the crude product from methylene chloride/ether, 17.8 g. of the methyl ester of 17β-hydroxy-3,20-dimethoxy-3,5-pregnadiene-21-oic acid is obtained, m.p. 182°–185°.

EXAMPLE 4

21-Acetoxy-20-methoxy-4,16-pregnadien-3-one (a) 3,20-Dimethoxy-3,5-pregnadiene-17β,21-diol A solution of 7.8 g. of the methyl ester of 17β-hydroxy-3,20-dimethoxy-3,5-pregnadiene-21-oic acid in 145 ml. of toluene is combined at −20° dropwise with 60 ml. of a 20% solution of diisobutyl aluminum hydride in toluene. Thereafter, the mixture is agitated for 60 minutes at 0°, excess hydride is then decomposed by adding 5 ml. of ethyl acetate and 20 ml. of water, and the mixture is filtered and the filtrate concentrated under vacuum. Yield: 7.2 g. of 3,20-dimethoxy-3,5-pregnadiene-17β,21-diol, m.p. 152°–155°.

(b) 21-Acetoxy-17β-hydroxy-20-methoxy-4-pregnen-3-one

A solution of 7.2 g. of 3,20-dimethoxy-3,5-pregnadiene-17β,21-diol in 30 ml. of acetic anhydride and 10 ml. of pyridine is agitated for 60 minutes at room temperature. To work up the reaction mixture, the latter is poured into 200 ml. of water and stirred for 30 minutes at 50°. After cooling, the mixture is extracted with ethyl acetate, washed neutral with saturated $NaHCO_3$ solution, dried over $Na_2SO_4$, and concentrated, thus obtaining 6.4 g. of 21-acetoxy-17β-hydroxy-20-methoxy-4-pregnen-3-one, m.p. 145°–147°.

(c) 21-Acetoxy-20-methoxy-4,16-pregnadien-3-one

A solution of 5 g. of 21-acetoxy-17β-hydroxy-20-methoxy-4-pregnen-3-one and 2.4 g. of methanesulfonic acid chloride in 80 ml. of methylene chloride is combined dropwise at −30° with 1.6 ml. of triethylamine. The mixture is stirred for 15 minutes at −30°, poured into 200 ml. of water, and extracted with methylene chloride, thus obtaining 4.6 g. of 21-acetoxy-20-methoxy-4,16-pregnadien-3-one, m.p. 115°–157°.

EXAMPLE 5

Methyl Ester of 17β-Hydroxy-3,20-dimethoxy-19-nor-1,3,5(10)-pregnatriene-21-oic Acid Under ice cooling, 4.6 ml. of a 15% solution of n-butyllithium in hexane is added dropwise to a solution of 1.1 g. of diisopropylamine in 10 ml. of tetrahydrofuran; then, the mixture is stirred for 10 minutes at 25°. Thereafter, the reaction mixture is cooled to −78° with acetone/$CO_2$ and, over a period of 5 minutes, 1.0 g. of the methyl ester of methoxyacetic acid in 2 ml. of THF is added dropwise to the reaction solution. The mixture is then agitated for another 10 minutes at −78°. Then, a solution of 500 mg. of estrone methyl ether in 13 ml. of THF is added dropwise thereto and the mixture is stirred for another 3 hours at −78°. For working-up purposes the reaction mixture is combined at −50° dropwise with 10 ml. of saturated $NH_4Cl$ solution, then poured into about 100 ml. of water, and extracted with ethyl acetate. The crude product is recrystallized from ether, thus obtaining 0.68 g., m.p. 152°–154°.

EXAMPLE 6

Methyl Ester of 3,20-Dimethoxy-19-nor-1,3,5(10),17(20)-pregnatetraene-21-oic Acid Under ice cooling, 7.6 ml. of thionyl chloride is added dropwise to a solution of 15.0 g. of 17β-hydroxy-3,20-dimethoxy-19-nor-1,3,5(10)-pregnatriene-21-oic acid methyl ester in 75 ml. of pyridine. The mixture is then agitated for 30 minutes at 0°. To work the mixture up, it is poured into 200 ml. of water, extracted with ethyl acetate, the ethyl acetate phases washed with 2N HCl and saturated NaCl solution, dried over $Na_2SO_4$, and concentrated, thus obtaining 12.4 g., m.p. 129°–130° (diisopropyl ether).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of 17β-hydroxy-20-alkoxypregnane-21-oic acid derivatives of the formula

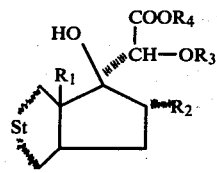

wherein
$R_1$ is methyl or ethyl;
$R_2$ is hydrogen or methyl, either being in the α- or β-position;
$R_3$ is lower alkyl of 1-4 carbon atoms;
$R_4$ is alkyl of 1-8 carbon atoms or benzyl; and
St is the residue of a steroid ABC ring system;
which comprises reacting, at −80° to −20° C.,
(a) a 17-oxo compound of the formula

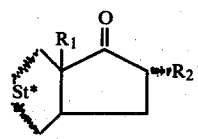

wherein
$R_1$ and $R_2$ are as defined above and
St* is said steroid ABC ring system residue, St, in a form which is chemically acceptable with said reaction;
with (b) an enolate ion of an alkoxyacetic acid alkyl ester of the formula

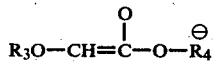

wherein $R_3$ and $R_4$ are as defined above.

2. The process of claim 1, wherein the moiety St contains oxo groups and in the moiety St* said oxo groups are blocked by protecting groups.

3. The process of claim 1, wherein the process is carried out in an inert solvent.

4. The process of claim 1, wherein $R_3$ is methyl.

5. The process of claim 1, wherein $R_4$ is methyl or ethyl.

6. The process of claim 1, wherein St is substituted by F, Cl, $CH_3$, free, esterified or etherified OH, or free or ketalized oxo.

7. The process of claim 1, wherein St contains $\Delta^4$, $\Delta^{1,4}$, $\Delta^{4,6}$, $\Delta^{4,9}$, $\Delta^{4,11}$, $\Delta^{1,4,9}$, $\Delta^{1,4,11}$, $\Delta^5$, $\Delta^{5,9}$, $\Delta^{5,11}$, $\Delta^{1,3,5}$, $\Delta^{1,3,10}$, $\Delta^{1,3,5,9}$, $\Delta^{1,3,5,11}$, $\Delta^{1,3,10,11}$, $\Delta^{1,3,10,9}$, $\Delta^3$, $\Delta^{2,5}$, $\Delta^{2,10}$, $\Delta^{2,5,9}$, $\Delta^{2,10,9}$, $\Delta^{3,5}$, $\Delta^{3,5,9}$ or $\Delta^{3,5,11}$ double bonds.

8. The process of claim 1, wherein St is one of of formulae $St_1$ through $St_6$

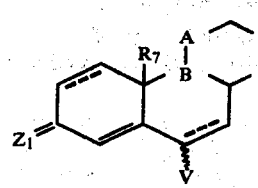

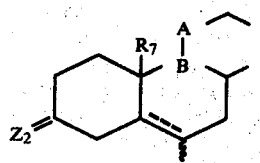

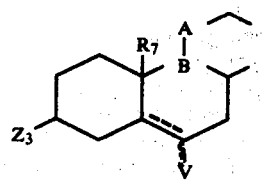

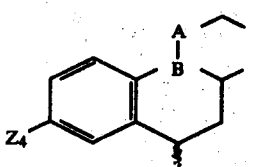

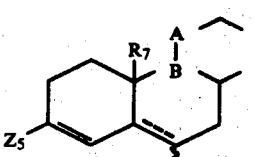

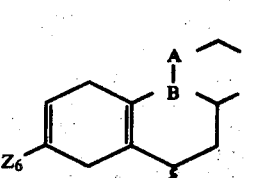

wherein
the grouping —A—B— is a —$CH_2$—CH<, —CHF—CW<, —CHCl—CW<, —CHOH—CW<, —CO—CW<, or —CH=C<-group wherein W is hydrogen, fluorine or chlorine;
V is hydrogen, methyl, or fluorine;
$Z_1$ is free or ketalized oxo;
$Z_2$ is ketalized oxo;
$Z_3$ and $Z_4$ each is free, esterified, or etherified hydroxy;
$Z_5$ and $Z_6$ each is etherified hydroxy;
$R_7$ is hydrogen or methyl; and the bonds, ———, are single bonds or double bonds.

9. The process of claim 1, which further comprises dehydrating the product of the reaction of (a) with (b) to obtain the corresponding 17,20-enol ether.

10. The process of claim 1, which further comprises reducing the product of the reaction of (a) with (b) to the corresponding 21-alcohol.

* * * * *